United States Patent
Prisner et al.

(10) Patent No.: US 8,823,373 B2
(45) Date of Patent: *Sep. 2, 2014

(54) DUAL-RESONANCE STRUCTURE AND METHOD FOR EXAMINING SAMPLES USING A PLURALITY OF CONDUCTIVE STRIPS

(75) Inventors: Thomas Prisner, Bad Vilbel (DE); Vasyl Denysenkov, Frankfurt am Main (DE)

(73) Assignee: Johann Wolfgang Goethe-Universität Frankfurt am Main, Frankfurt am Main (DE)

( * ) Notice: Subject to any disclaimer, the term of this patent is extended or adjusted under 35 U.S.C. 154(b) by 186 days.

This patent is subject to a terminal disclaimer.

(21) Appl. No.: 13/262,411

(22) PCT Filed: Mar. 16, 2010

(86) PCT No.: PCT/EP2010/001651
§ 371 (c)(1),
(2), (4) Date: Nov. 30, 2011

(87) PCT Pub. No.: WO2010/112137
PCT Pub. Date: Oct. 7, 2010

(65) Prior Publication Data
US 2012/0068706 A1    Mar. 22, 2012

(30) Foreign Application Priority Data
Apr. 3, 2009 (WO) .................. PCT/EP2009/002488
Oct. 8, 2009 (DE) ........................ 10 2009 048 636

(51) Int. Cl.
| | |
|---|---|
| G01R 33/46 | (2006.01) |
| G01R 33/34 | (2006.01) |
| G01R 33/28 | (2006.01) |
| G01R 33/62 | (2006.01) |
| G01R 33/345 | (2006.01) |
| G01N 24/12 | (2006.01) |

(52) U.S. Cl.
CPC .............. *G01N 24/12* (2013.01); *G01R 33/282* (2013.01); *G01R 33/62* (2013.01); *G01R 33/345* (2013.01)
USPC ........................... 324/309; 324/307; 324/322

(58) Field of Classification Search
USPC .......................................................... 324/309
See application file for complete search history.

(56) References Cited

U.S. PATENT DOCUMENTS

| | | | |
|---|---|---|---|
| 4,751,464 A * | 6/1988 | Bridges | 324/318 |
| 5,621,322 A | 4/1997 | Ehnholm | 324/318 |

FOREIGN PATENT DOCUMENTS

| | | |
|---|---|---|
| DE | 10 2008 017 135 A1 | 11/2009 |
| JP | 2005121409 | 5/2005 |

OTHER PUBLICATIONS

Lee et al., "Planar strip array (PSA) for MRI"; Mar. 27, 2001; Magnetic Resonance in Medicine, vol. 45, Issue 4, pp. 673-683.*

(Continued)

*Primary Examiner* — Melissa Koval
*Assistant Examiner* — Rishi Patel
(74) *Attorney, Agent, or Firm* — Sunstein Kann Murphy & Timbers LLP (57) ABSTRACT

A double-resonance structure 10 for DNP-NMR and/or ENDOR experiments is described. The double-resonance structure 10 comprises a microwave resonator 30 for generating electromagnetic field suitable for EPR, and an HF resonator 12 for generating electromagnetic fields suitable for NMR. The HF resonator 12 comprises a plurality of electrically conductive strips 14, which are electrically connected so that an HF current can be generated in the plurality of strips 14 such that the HF currents flow in the same direction in the individual strips 14 at the same time. A section of the HF resonator 12 at the same time forms a part of the microwave resonator 30.

30 Claims, 4 Drawing Sheets (56) References Cited

OTHER PUBLICATIONS

Avdievich et al. "Multifrequency Probe for Pulsed EPR and ENDOR Spectroscopy"; Nov. 7, 2001; Journal of Magnetic Resonance, 153, pp. 175-185.*

Matsumoto, S., Nagai, M., Yamada, K., Hyodo, F., Yasukawa, K., Muraoka, M., Hirata, H., Ono, M. and Utsumi, H. (2005), A composite resonator assembly suitable for EPR/NMR coregistration imaging. Concepts Magn. Reson., 25B: 1-11. doi: 10.1002/cmr.b.20028.*

Weis, V., et al., "High-Field DNP and ENDOR With a Novel Multiple-Frequency Resonance Structure," *Journal of Magnetic Resonance*, 140, pp. 293-299, 1999.

Wallace, W.J., et al., "Microstrip Resonators for Electron-Spin Resonance," *Rev. Sci. Instrum.*, vol. 62, No. 7, pp. 1754-1766, Jul. 1991.

Sloop, D., et al., "Spin-Echo-ENDOR Studies of the Photoexcited Triplet State of Pentacene in p-Terphenyl Crystals at Room Temperature," *Journal of Magnetic Resonance*, vol. 86, No. 1, pp. 156-159, Jan. 1990.

Singel, D.J., et al., "A Spectrometer for EPR, DNP, and Multinuclear High-Resolution NMR," *Journal of Magnetic Resonance*, vol. 81, No. 1, pp. 145-161, Jan. 1989.

Johansson B., et al., "A Stripline Resonator for ESR," *Rev. Sci. Instrum.*, vol. 45, No. 11, pp. 1445-1447, Nov. 1974.

Denysenkov, V., et al., "New Double Resonance Structures for High Field DNP in Liquids," *Institute of Physical and Theoretical Chemistry*, Oral Presentations, 1 page.

Burghaus, O., et al., "A Novel High-Field/High Frequency EPR and ENDOR Spectrometer Operating at 3 mm Wavelength," *Meas. Sci Technol.*, vol. 3, pp. 765-774, 1992.

Bennati, M., et al., "Pulsed Electron-Nuclear Double Resonance (ENDOR) at 140 Ghz," *Journal of Magnetic Resonance*, vol. 138, pp. 232-243, 1999.

Bauer, C., et al., "Design of a Permanent Magnet With a Mechanical Sweep Suitable for Variable-Temperature Continuous-Wave and Pulsed EPR Spectroscropy," *Journal of Magnetic Resonance*, vol. 198, pp. 222-227, 2009.

Becerra et al., "A Spectrometer for Dynamic Nuclear Polarization and Electron Paramagnetic Resonance at High Frequencies," *J Magn. Reson. Ser. A*, vol. 117, No. 1, pp. 28-40 (Nov. 1995).

* cited by examiner

DUAL-RESONANCE STRUCTURE AND METHOD FOR EXAMINING SAMPLES USING A PLURALITY OF CONDUCTIVE STRIPS

FIELD OF THE INVENTION

The present invention relates to a double-resonance structure for DNP and/or ENDOR experiments. Furthermore, it relates to a method for investigating samples by DNP and/or ENDOR as well as a DNP-NMR spectrometer, an ENDOR spectrometer and a combined DNP-NMR/ENDOR spectrometer.

BACKGROUND OF THE INVENTION

Nuclear magnetic resonance (NMR) spectroscopy (NMR spectroscopy) is one of the most important spectrographic methods for elucidating the structure and dynamics of molecules, in particular in organic chemistry and biochemistry. However, the sensitivity of NMR spectrometers reaches its limits in many applications, for example, in investigation of large biomolecules in vitro and in vivo. The lack of sensitivity can be improved to a certain extent by applying a higher external magnetic field, but this is possible only to a limited extent and involves very high efforts.

A very promising alternative for increasing the sensitivity of NMR measurements in biomolecules, for example, consists of a method known as "dynamic nuclear polarization" or the "DNP method" according to the abbreviation of the English term "dynamic nuclear polarization." DNP results from the transfer of the spin polarization of the electrons to the nuclei according to the principle also known as the "Overhauser effect." To make DNP usable in NMR spectroscopy, the electronic spin polarizations must first be transferred to the nuclear spin system. To do so, the sample is excited at an electronic spin resonance frequency, usually referred to as the EPR frequency, where EPR is the abbreviation for the English term "electronic paramagnetic resonance." The EPR frequency, also known as the Larmor frequency, corresponds to the splitting of the energy of electronic spin energy quantum states of an atom or molecule in an external magnetic field according to the Zeeman effect, which would degenerate without an external magnetic field. The splitting of the energy states is proportional to the strength B of the external magnetic field and thus the value of the EPR frequency is a function of the magnetic field strength. However, in applications that are of practical relevance, this is always in the microwave range. The change of the polarization of the electronic spin through input of EPR microwaves is often referred to graphically as "pumping."

The NMR signal gain due to DNP is proportional to the square of the intensity of the EPR microwave field as long as the EPR transitions are not saturated. To obtain an EPR microwave field with the highest possible power and/or field strength, microwave resonators in which the sample is arranged for stimulation of the EPR transitions are preferably used.

As in EPR, nuclear magnetic resonance (NMR) is also based on transitions between quantum states of a spin in an external magnetic field, with the difference being that energy splitting of the nuclear spin is much smaller than in EPR. The NMR frequencies are typically in a two-digit megahertz range, i.e., still in the high-frequency (HF) range. Instead of the term "high frequency," the literature also uses the term "radio frequency." The term "high frequency" should therefore not hide the fact that these NMR frequencies are of course the lower frequencies of the frequencies involved, namely lower than the aforementioned microwave frequencies.

Since a high-intensity HF field is also necessary for NMR spectroscopy, an HF resonator in the form of an HF resonance coil is generally also used. Therefore so-called double-resonance structures, which have a microwave (MW) resonator for EPR transitions and an HF coil for NMR transitions are available for DNP-NMR experiments, so that the same sample may be exposed simultaneously to an MW field and an HF field, each with a high intensity.

One method that is conceptually related to DNP-NMR spectroscopy is the so-called electron nuclear double-resonance spectroscopy, also known as ENDOR spectroscopy. ENDOR spectroscopy is a special type of EPR spectroscopy, in which NMR transitions in the sample are created by input of HF fields. To this extent, ENDOR spectroscopy is conceptually very similar to DNP-NMR spectroscopy, except that in this case, it is pumped using HF fields, and EPR spectroscopy is performed. A double-resonance structure is also used for ENDOR experiments.

RELATED PRIOR ART

A double-resonance structure is known from the article by Weis et al. (High-field DNP and ENDOR with novel multiple-frequency resonance structure, J. Magn. Reson. 140, 293-299 (1999)). This known double-resonance structure comprises a cylindrical microwave resonator formed by a helical conductive strip. The helical conductive strip forms a coil, which assumes the function of the HF resonator. The cylindrical MW resonator is therefore also referred to as a helix resonator. An iris through which microwaves can be fed into the helix resonator is formed in the lateral surface of the helix. The length of the resonator can be adjusted by adjustable pistons, which are inserted into both ends of the helix.

A cylindrical $TE_{011}$ microwave mode can be excited in the known helix resonator, so that a very high microwave energy density can be achieved in the MW resonator. However, the dimensions of the helix resonator correlate with the microwave wavelength, and if the microwave wavelength drops to less than one millimeter in strong magnetic fields according to the EPR conditions, then the small size of the helix resonator limits the sample volume that can be accommodated in the helix resonator.

In the case of liquid samples, in particular aqueous samples, there is also the problem in use of the known helix resonator that its volume, which is limited anyway, can not at all be fully utilized with the sample volume because the sample would heat up too much with the input of microwaves. The reason for the great heating is the frequency-dependant dielectric permittivity of water with input of microwaves. For example, the complex dielectric permittivity of water at a microwave frequency of 260 GHz has a real component $\varepsilon'=5.6$ and an imaginary component $\varepsilon''=5.8$, where the dielectric losses are proportional to the imaginary component $\varepsilon''$ of the permittivity. The relatively great losses, also known as "insertion losses," result in the MW field being much lower in the sample than that outside of the sample, on the one hand, and on the other hand, the sample being greatly heated.

For example, if biomolecules in aqueous solutions are to be investigated, high heating of the sample is out of the question because the biomolecules might be destroyed by the heating. The present inventors used an aqueous sample in a capillary with a diameter of only 0.1 mm in an experiment and found that the sample was heated by 90° C. when microwaves were injected. Even at a capillary diameter of only 0.05 mm, there was a heating of 17° C. This means that the sample volume must always be kept relatively small, so that the filling factor $$\eta = \frac{V_s \langle B_{HF}^2 \rangle_s}{V_{struk} \langle B_{HF}^2 \rangle_{struk}}$$

is relatively small here, leading to a reduced NMR sensitivity. Herein, $V_s$ is the volume of the sample, $\langle B_{HF}^2 \rangle_s$ is the average value of the HF magnetic field strength $B_{HF}$ in the range of the sample, $V_{struk}$ is the volume of the structure and $\langle B_{HF}^2 \rangle_{struk}$ is the average value of the magnetic field strength $B_{HF}$ of the field in the range of the structure. If the MW power is reduced to prevent excessive heating of the sample, this leads to a reduction in the DNP and this in turn has a deleterious effect on NMR sensitivity.

Another double-resonance structure, a so-called cavity resonator for ENDOR, is described in JP2005-121409. The resonator uses an HF coil, wound around the sample, which is in turn arranged in an MW cavity. This structure is suitable for ENDOR spectroscopy but not for DNP applications because the HF coil leads to a disturbance in the distribution of the electrical MW field over the sample volume, in turn leading to a disadvantageous heating of the sample.

Figure 3:
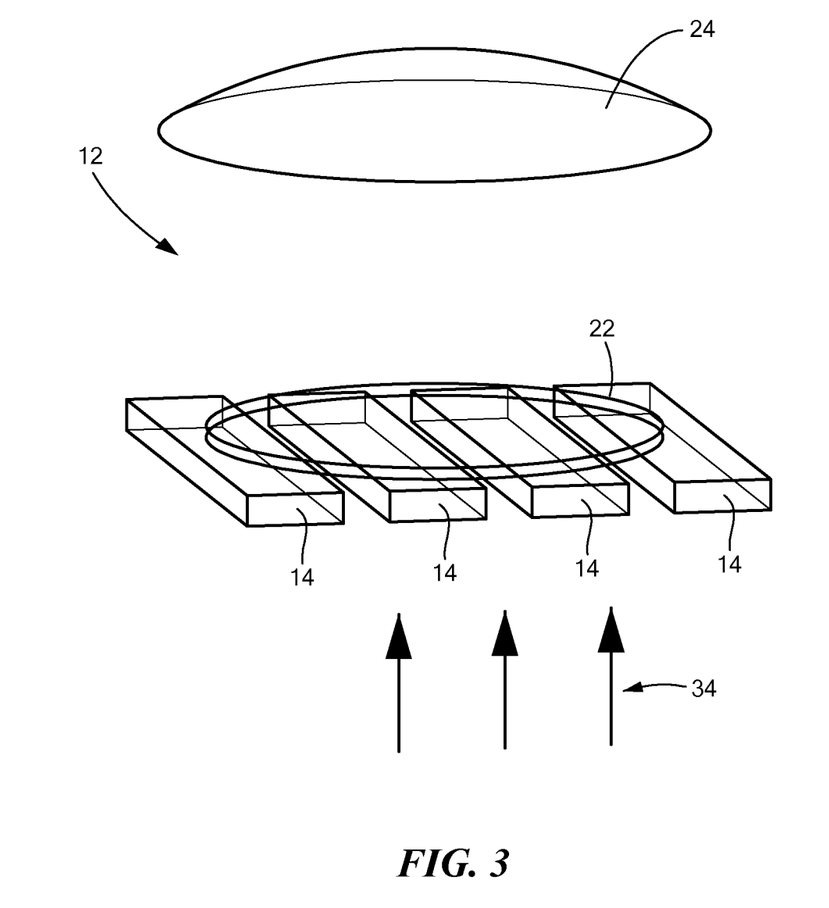
FIG. 3 shows a perspective view of an alternative embodiment of the double-resonance structure, in which the microwaves are input between the conductive strips of the HF resonator.

Three further DNP and EPR spectrometers are known from Becerra L. R. et al.: "A Spectrometer for Dynamic Nuclear Polarization and Electron Paramagnetic Resonance at High Frequencies," Journal of Magnetic Resonance, Series A, 1995, vol. 117, pp. 28-40. FIG. 3 of this article shows a first spectrometer with a rotating sample, in which microwave radiation is fed into the sample in the direction of the axis of rotation of the sample, using a waveguide. The entire sample is surrounded by a coil, forming an NMR resonator.

Figure 4:
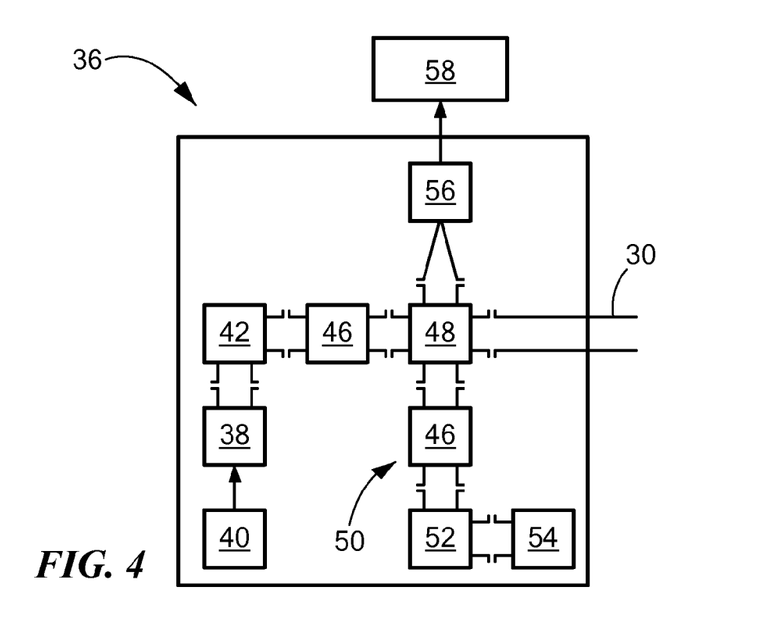
FIG. 4 shows a schematic diagram of the components of a microwave bridge.

FIG. 4 shows a second static DNP arrangement, in which a Fabry-Perot mirror and a waveguide are opposite one another, forming a microwave resonator. To generate an NMR field, a coil forming an HF resonator is provided. The microwaves are input into the Fabry-Perot resonator between two coil windings. Finally, FIG. 7 of this article discloses a third double-resonance structure having a cylindrical microwave resonator and a coil forming an HF resonator, its longitudinal axis being arranged perpendicularly to the longitudinal axis of the microwave resonator.

In all three embodiments, the HF resonator is formed by a coil. Furthermore, in all three embodiments, the microwave resonator and the HF resonator are each structurally and functionally separate parts, which do not share any common components. Only the third embodiment is suitable for ENDOR experiments.

The patent application DE 10 2008 017 135, which was not published prior to this application, describes a double-resonance structure in which the HF resonator is formed by a strip resonator, one portion of the strip resonator at the same time forming a part of the microwave resonator.

SUMMARY OF THE INVENTION

The object of the present invention is to provide a double-resonance structure and a method for investigating specimens by means of DNP-NMR and/or ENDOR, which will allow an increased measurement sensitivity.

This object is achieved by a double-resonance structure and a method. The method is generally known from the prior art, but is characterized by the use of the inventive double-resonance structure. Advantageous further embodiments are provided in the dependent claims.

The double-resonance structure of the invention differs from that according to the prior art in that the HF resonator comprises a plurality of electrically conductive strips, which are arranged side by side and are connected electrically, so that an HF current can be generated in the plurality of strips. The HF currents in the individual strips are flowing in the same direction at the same time, such that a portion of the HF resonator simultaneously forms a part of the microwave resonator.

HF fields for NMR transitions of sufficient strength can be created by the HF currents in the conductive strips. At the same time, the strips form a portion or section of the microwave resonator. The microwave frequencies relevant here are so-called "quasi-optical" microwaves, and the conductive strips of the HF resonator arranged side by side form a reflector or mirror for the microwave resonator on which the microwaves are quasi-optically reflected. This creates a more open structure in comparison with the helix resonator, this open structure being advantageous with regard to dissipation of heat and permitting the use of larger sample volumes than are possible with the known helix resonator.

The double-resonance structure according to the invention also differs from the double-resonance structure known from DE 10 2008 017 135, which was not published prior to the present application, in that instead of a strip-shaped HF resonator, a plurality of strips arranged side by side are used, but the HF current flows in the same direction in these strips. The width of the individual strips may therefore be selected to be much smaller than if just a single strip resonator were used, and at the same time it is possible to ensure that the total width of the HF resonator is large enough to form a microwave reflector of sufficient size for the microwave resonator.

The advantage of using narrower strips is that the so-called "conversion factor" of the HF resonator is increased. The conversion factor is a proportionality factor between the magnetic field strength achievable with the resonator and the square root of the supplied power, so that a higher conversion factor permits a higher magnetic field strength. Likewise, an elevated conversion factor leads to an increased NMR measurement sensitivity. Since the conversion factor is limited significantly by the width of the strip resonator, it is advantageous to arrange a plurality of narrower conductive strip resonators side by side instead of one wider strip resonator, so that they can serve jointly as a reflector for microwaves as part of the microwave resonator.

The plurality of conductive strips is preferably arranged parallel to one another in the form of a grid. The distance between neighboring conductive strips is preferably smaller than the strip width and in particular is less than half the strip width. It has been found that a grid formed of conductive strips in fact allows a much higher conversation factor than a single strip resonator of the same total width, and that the grid formed from the conductive strips is at the same time suitable as a reflector for the MW resonator.

The conductive strips may be made of a metal of a high conductivity. However, in a preferred embodiment, they are made of a composite material, whose magnetic susceptibility is matched to that of a sample to be investigated.

At least some of the conductive strips are preferably connected in series by using additional conductors. A first end of the series of series-connected strips is preferably connected to ground potential. Furthermore, a second end of the series of series-connected strips is preferably connected or connectable via a capacitor, in particular an adjustable matching capacitor to an HF source and/or an HF receiver for generating and/or detecting an NMR signal.

In an advantageous further embodiment, the MW resonator comprises a spherical reflector and the planar reflector, which are opposite one another, such that the planar reflector is formed by a section or portion of the HF resonator. Such an MW resonator is also known as a "semiconfocal Fabry-Perot resonator." In this arrangement, the HF resonator has three functions:

Firstly, it generates an HF field, whose magnetic field strength $B_{HF}$ is greater than that of a known helix resonator and is greater than that of an embodiment (not published previously) having a single strip resonator. This permits a higher NMR sensitivity.

Secondly, the conductive strips arranged side by side serve jointly as reflectors for the MW resonator, so that the different resonators can be combined ideally without mutually impairing their respective functions. The resulting structure offers enough space for sample volumes which may be larger by a factor of ten than is the case with the helix resonator generally used.

And thirdly, the multiple conductive strips together act as a heat sink, by means of which heat generated in particular by irradiating an aqueous sample with microwaves can be dissipated, so that even relatively large sample volumes may be used without excessive heating.

An iris, through which microwaves can be fed into the MW resonator, is preferably formed in the spherical reflector. The iris may be a slotted iris, in order to generate linearly polarized microwaves in the MW resonator. Alternatively, the iris may be designed in the form of a circle in order to generate circularly polarized microwave modes in the MW resonator.

Alternatively, however, the microwaves may also be fed into the MW resonator by introducing them between the conductive strips of the HF resonator. A horn radiator is preferably provided for this purpose, arranged on the side of the HF resonator facing away from the MW resonator, so that it can input microwaves into the microwave resonator through interspaces between the conductive strips of the HF resonator. Microwaves having a Gaussian intensity profile are preferably used here for this input.

The spherical reflector and the planar HF resonator are preferably designed and arranged so that a $TEM_{00n}$ microwave mode can be formed between them. The microwave resonator is preferably also connected to a microwave source, which can be operated in the lowest radiation mode of the MW resonator.

In the double-resonance structure, a location for receiving a sample, which has a thermally conductive connection to the HF resonator is preferably provided. The HF resonator therefore serves as a heat sink for the sample at the same time, so that the problem of heating of the sample due to the interaction with microwave radiation can be reduced significantly and larger sample volumes can be used while achieving the same absolute heating.

The location for receiving a sample preferably includes a device for holding a liquid sample, where the level of the liquid sample to be held is preferably up to one-tenth of the resonant wavelength of the microwave resonator. The sample may therefore be limited to areas in which the electric component of the standing microwave is relatively small, so that excessive heating of the sample can be prevented, as explained in greater detail below on the basis of an exemplary embodiment.

In an advantageous embodiment, the double-resonance structure is embodied as a probe and/or as a probe head, which can be inserted into a borehole in a magnet. This magnet, into which the probe head can be inserted, is intended for generating a static magnetic field in which the essentially degenerate quantum states of the sample are split by interaction of the electronic spin and/or nuclear spin with the external static magnetic field. The probe head preferably has a housing, which is connected to ground potential.

The double-resonance structure described here may be embodied further to form a DNP-NMR spectrometer. To do so, a microwave source, which is connected to the double-resonance structure for input of microwaves into the MW resonator, and an NMR device, which is connected to the double-resonance structure for input of HF signals into the HF resonator and for receiving HF signals from the HF resonator, are provided.

Likewise, the double-resonance structure according to the invention may be further embodied to form an ENDOR spectrometer, in which a microwave source, which is connected to the double-resonance structure for input of microwaves into the MW resonator and for receiving MW signals from the MW resonator, and an HF source, which is connected to the double-resonance structure for input of HF signals into the HF resonator, are provided. Furthermore, the double-resonance structure according to the invention may be used in a combined DNP-NMR/ENDOR spectrometer, which is capable of both operating modes.

BRIEF DESCRIPTION OF THE FIGURES

Figure 1:
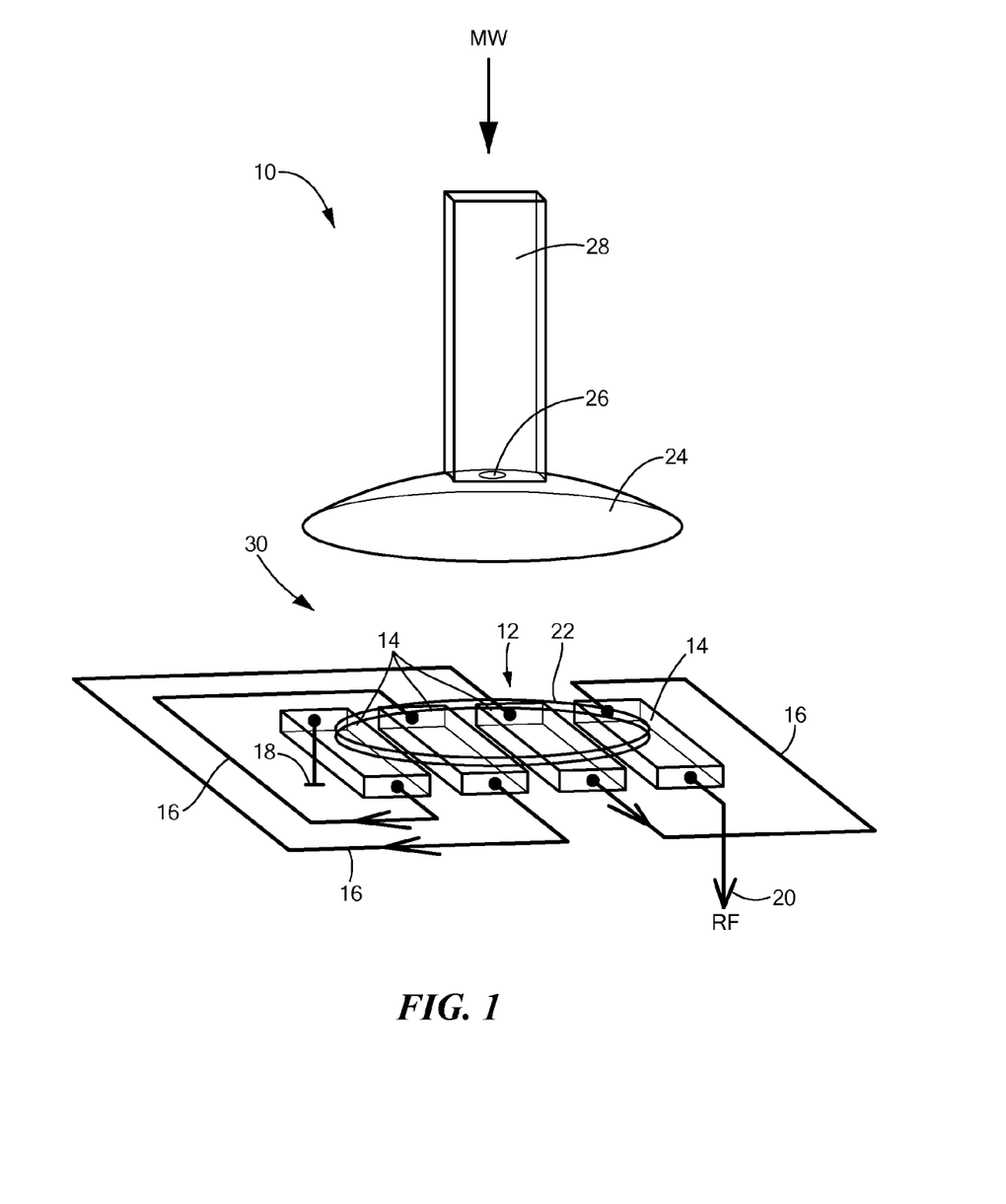
FIG. 1 shows a perspective view of the resonance structure according to a further embodiment of the invention.
Figure 2:
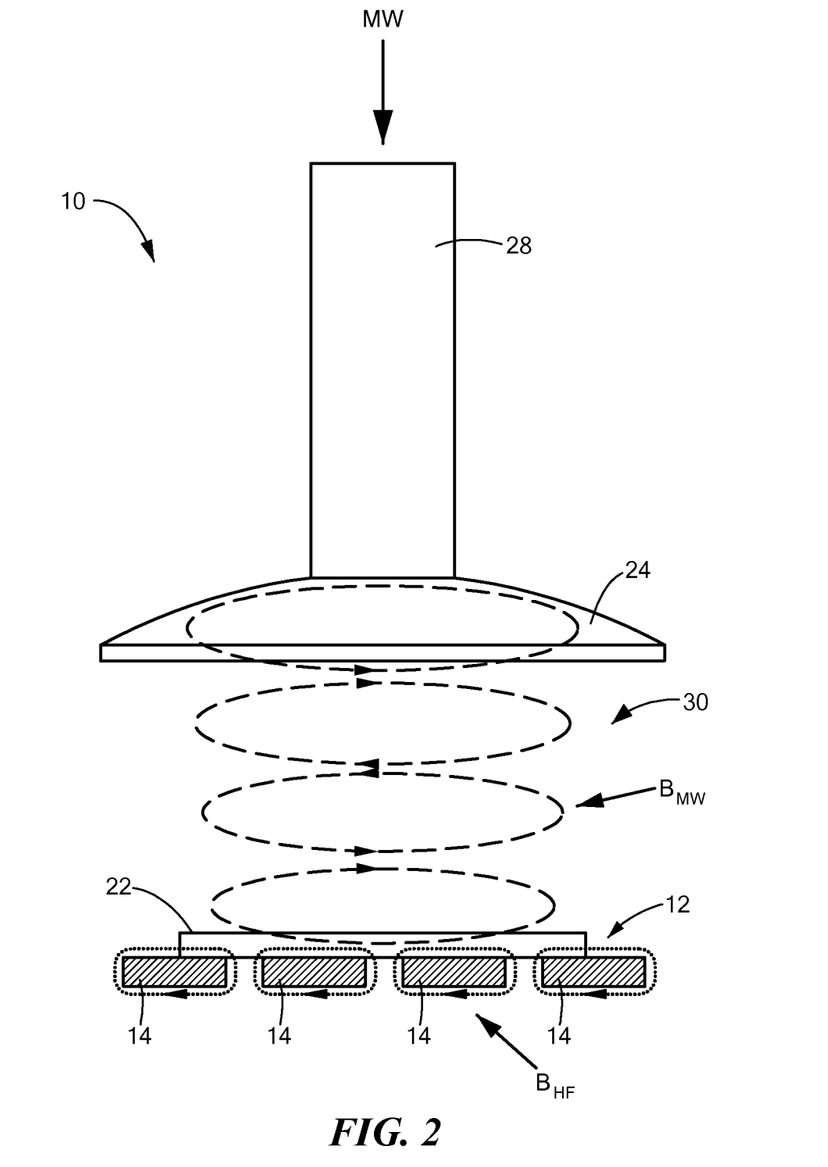
FIG. 2 shows a side view of the double-resonance structure from FIG. 1, showing magnetic field lines $B_{HF}$ of the HF field and magnetic field lines $B_{MW}$ of the MW field.

Additional advantages and features of the devices of the method according to the present invention are derived from the following description, in which the invention is explained in greater detail on the basis of one exemplary embodiment with reference to the accompanying drawings, in which:

FIG. 1 shows a double-resonance structure 10 in a perspective view, in which the individual components are shown as transparent. FIG. 2 shows a side view of the same double-resonance structure 10, showing magnetic field lines $B_{HF}$ and $B_{MW}$ of the HF field and of the microwave field, respectively.

The double-resonance structure 10 comprises an HF resonator 12, which consists of several conductive strips 14 (four in the exemplary embodiment shown here) arranged parallel to one another and side by side in a plane. The conductive strips 14 of the HF resonator 12 are connected in series by additional conductors 16. A first end 18 of the series of series-connected strips 14 is connected to ground potential. A second end 20 of the series of series-connected conductive strips 14 is connectable to an HF source (not shown) or to an HF receiver (not shown) for generating and/or detecting an NMR signal. A capacitor (not shown in the figures), in particular an adjustable matching capacitor, may also be provided between the HF resonator 12 and the HF source and/or the HF receiver.

The conductive strips 14 of the HF capacitor 12 are connected by the additional conductors 16 so that the current flow in the conductive strips is always directed in the same direction.

A device 22 in the form of a flat container for receiving a liquid sample is arranged on the conductive strips 14. The container 22 is situated directly on the conductive strips 14 and is thus connected to them in a thermally conducting manner. The container 22 may serve to receive an aqueous sample, for example, which contains biomolecules to be investigated. The conductive strips 14 may be produced from a conductive composite material, whose magnetic susceptibility is matched to the magnetic susceptibility of the samples to be investigated using the double-resonance structure 10.

A spherical reflector 24 in which an iris 26 is formed is situated above the HF resonator 12. The spherical reflector 24 is connected to a waveguide 28 by means of which microwaves can be fed into the interspace between the HF resonator 12 and the spherical reflector 24. The iris 26 may be slotted, to generate linearly polarized microwave modes, or may be circular to generate circularly polarized microwave modes.

The spherical reflector 24 and the HF reflector 12 together form a microwave resonator 30, which is also referred to as a semiconfocal Fabry-Perot resonator. The distance between the spherical reflector 24 and the HF resonator 12 is adjustable, so that the resonant frequency of the MW resonator 30 can be adjusted by varying the distance between the spherical reflector 24 and the HF resonator 12.

The function of the double-resonance structure 10 of FIG. 1 and FIG. 2 is described below:

The term "double-resonance" indicates that resonance conditions for two different electronic fields are created in the area of the sample holder 22. One resonance relates to the resonance of the HF resonator 12, which is operated at a frequency corresponding to an NMR resonance in an external magnetic field $B_0$. At an external magnetic field $B_0$ of approx. 10 T, the NMR frequency amounts to approx. 400 MHz, for example. The field lines in the high-frequency magnetic field $B_{HF}$, which is generated by the individual conductive strips 14 of the HF resonator, are diagramed schematically in FIG. 2.

The second resonance of the double-resonance structure relates to a resonance in the microwave range, namely at frequencies which correspond to EPR transitions. At an external magnetic field $B_0$ of approx. 10 T, the EPR resonant frequency is approx. 260 GHz. $TEM_{00n}$ modes, where n is an integer, can be generated in the MW resonator 30. The $TEM_{00n}$ modes are axially symmetrical, and the field profile in a plane parallel to the surface of the HF resonator 12 has a Gaussian shape, with a width which depends on the distance from the spherical reflector 24.

The magnetic field $B_{MW}$ of such a mode is shown schematically in FIG. 2. The highest magnetic field strength of the MW magnetic field $B_{MW}$ occurs directly at the surface of the HF resonator, i.e., at the surface of the conductive strips 14, i.e., where the sample holder 22 is arranged. The next maximum of the magnetic field strength $B_{MW}$ is located half a wavelength above the surface of the HF resonator 12. The sample holder 22 is therefore selected to be so shallow that the maximum thickness of the samples amounts to approx. 10% of the resonant wavelength of the microwave field. At a greater thickness of the sample, this would also be in the range of the standing microwave with a high electric field, so that the sample would be excessively heated and furthermore the quality factor Q of the WM resonator 30 would be impaired.

Since the sample holder 22 is arranged directly on the conductive strips 14 of the HF resonator 12, heat can be dissipated from the sample in this way. This is a particular advantage in comparison with a helix resonator, for example, for which heating because of microwave absorption is difficult to prevent, and which would be only possible with very small sample volumes and a low microwave power, which however reduces the measurement accuracy.

DNP-NMR experiments or ENDOR experiments utilizing the double-resonance can be performed. In DNP-NMR experiments, electronic spins in the sample are polarized by the microwave field, and this polarization is transferred to the nuclear spins according to the Overhauser effect, resulting in a higher NMR signal in measurement of NMR spectra. In ENDOR experiments, the reverse case occurs: The sample is excited with NMR frequencies and EPR spectra are measured. The double-resonance structure 10 is suitable for both types of experiments and may thus be used as a probe or probe head for both an ENDOR spectrometer and for a DNP-NMR spectrometer. It can also be used with a suitable microwave bridge, which is connected to the microwave waveguide 28, and a suitable NMR device, which is connected to the second end 20 of the series connection of the HF resonator 12, in a combined ENDOR/DNP-NMR spectrometer, which may optionally be operated in each of these modes.

As shown in FIGS. 1 and 2, the HF resonator 12 is composed of a plurality of conductive strips 14 arranged side by side, the width of each being relatively small in comparison with the total width of HF resonator 12. Due to the small width of the conductive strips 14 of the HF resonator 12, the conversation factor of the HF resonator 12 can be increased significantly in comparison with an embodiment using a single conductive strip of the same total width. Since the HF resonator 12 at the same time serves as a planar reflector of the MW resonator 30, in the case of an HF resonator with just one strip whose width cannot be reduced at will, the microwave losses would be too great otherwise. However, it has been found that the conductive strips 14, which are arranged side by side in the manner of a grid, form a planar MW reflector of a sufficient quality on the whole to create a functional MW resonator 30, while at the same time reducing the width of the individual strips 14 in turn leads to an increased conversion factor.

In the final effect, an HF resonator with an increased conversion factor and thus an increased magnetic field $B_{HF}$ and an increased NMR sensitivity can thus be achieved, at the same time being part of a fully functional MW resonator.

FIG. 3 shows a schematic diagram of an alternative embodiment of a double-resonance structure 32. The design of the double-resonance structure 32 is basically very similar to that of the double-resonance structure 10 of FIGS. 1 and 2, so that the same reference numerals are used for corresponding components. It should be noted that the additional conductors 16 for connecting the conductive strips 14 are also present in the double-resonance structure 32 of FIG. 3 but have not been shown in this figure for the sake of simplicity.

The difference in the embodiment of FIG. 3 is that in the double-resonance structure 32, the microwaves are not input through an iris in the spherical reflector 24. Instead of that, the microwaves are input into the MW resonator 30 through the interspaces between the conductive strips 14 of the HF resonator 12. For example, microwaves in the form of a Gaussian beam 34 may be input from beneath the HF resonator 12, for example, with the help of a horn radiator (not shown).

Figure 5:
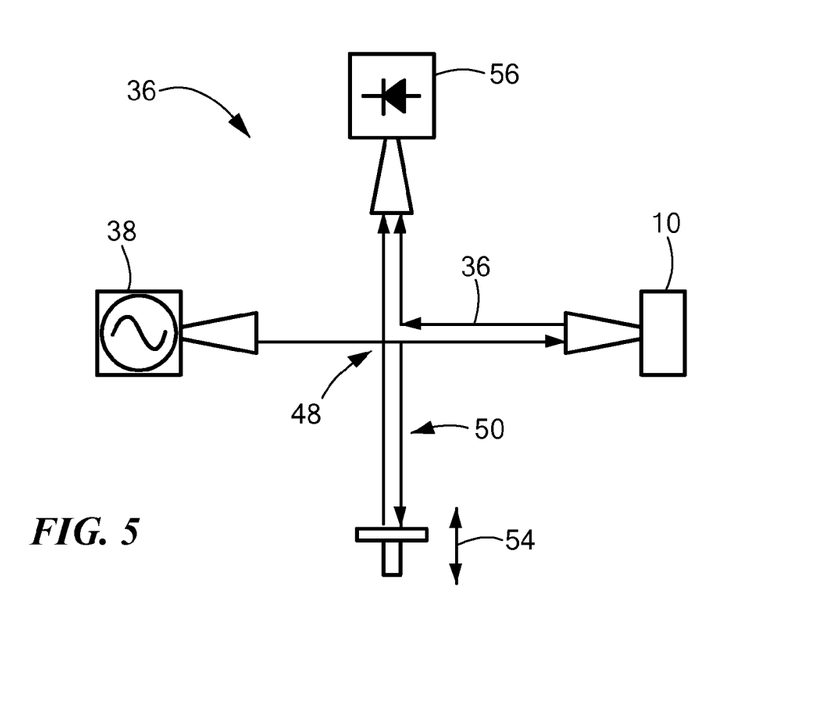
FIG. 5 shows a functional diagram of the microwave bridge from FIG. 4.

An example of a suitable microwave bridge 36 is shown in FIGS. 4 and 5. FIG. 4 shows the essential components of the microwave bridge 36 in a block diagram, and FIG. 5 shows the functional design of the microwave bridge 36.

As shown in FIG. 4, the microwave bridge 36 comprises a microwave oscillator 38, which is connected to a power supply 40. Furthermore, the microwave bridge 36 comprises a mechanical microwave switch 42 and an attenuator 46. A beam splitter 48 is provided to split the microwave signal between a signal arm, namely the microwave waveguide 30, which is connected to the double-resonance structure 10, and a reference arm 50, which consists of another attenuator 46, a wave-measuring device 52 and an adjustable reflector 54. Furthermore, the microwave bridge 36 comprises a detector 56, which is connected to a lock-in amplifier 58. The corresponding components in FIG. 5 are labeled with the same reference numerals.

The microwave bridge 36 of FIGS. 4 and 5 may be operated in an EPR detection mode and in a DNP mode. To do so, the microwave bridge 36 is designed as a Michelson interferometer, as is shown especially well in FIG. 5, where EPR spectroscopy is performed with the help of a signal of the microwaves reflected by the microwave resonator 32. The highest EPR sensitivity can be achieved when the beam splitter 48 directs half of the incident power into the reference arm 50 and into the signal arm, i.e., the microwave waveguide 30. However, this splitting of the power is not optimal for the DNP mode, because in the DNP mode as much microwave power as possible should be fed into the double-resonance structure, i.e., into the signal arm. To this end, the beam splitter 48 may be replaced by an alternative beam splitter, which allows 99.5% of the power to pass into the signal arm (waveguide 30), for example, and deflects only 0.5% of the power into the reference arm 50.

In the DNP-NMR mode, the HF terminal 20 of the double-resonance structure 10 is connected to a prior art NMR device, a so-called NMR console. In the ENDOR mode, the HF terminal 20 is connected to a suitable HF source instead of to the NMR console.

As shown in the above exemplary embodiments, the double-resonance structures 10, 32 of the present invention allow DNP-NMR and ENDOR experiments with very strong NMR and EPR fields and comparatively large sample volumes. In fact, the sample volumes which can be used are approximately ten times as large as with the helix resonator known from the state of the art and described in the introduction here. One particular advantage of the double-resonance structure 10 is that it is able to dissipate heat from the sample very effectively, so that biomolecules in aqueous solution, for example, can be investigated despite the high absorbed microwave power without an unacceptable increase in the temperature of the sample. This makes the double-resonance structures 10, 32 extremely advantageous for investigating liquid and/or aqueous samples in particular. Another special advantage of the double-resonance structures 10, 32 lies in the especially high conversion factor of the HF resonator 12, which is made possible by using a plurality of relatively narrow conductive strips 14, which jointly form an MW reflector of a sufficient width for the MW resonator 30.

The double-resonance structure shown here is suitable in particular for structural analysis of biomolecules (2D-NMR), i.e., kinetic studies, because the measurement times are greatly reduced, the analysis of complex (bio)molecule mixtures, for example, the analysis of metabolites, the identification and monitoring of impurities and for ligand and biomarker screening. Furthermore, dynamic molecular interactions can be investigated in an advantageous manner with the double-resonance structures 10, 32. In addition, the double-resonance structure is suitable for use in 2D and 3D analyses of condensed material, for example, ordered crystals, lipid layers and membranes and for NMR microscopy.

In an ENDOR spectroscopy mode, the double-resonance structure can be used advantageously in investigating defects in semiconductors, chiralities and endohedral complexes (fullerenes).

LIST OF REFERENCE NUMERALS 10 double-resonance structure
12 HF resonator
14 conductive strip of the HF resonator
16 additional conductor
18 first end of the HF resonator 12
20 second end of the HF resonator 12
22 sample container
24 spherical reflector
26 iris
28 waveguide
30 MW resonator
32 double-resonance structure
34 microwave beam
36 microwave bridge
38 MW oscillator
40 voltage source
42 mechanical microwave switch
46 attenuator
48 beam splitter
50 reference arm
52 wave measuring device
54 reflector
56 detector
58 lock-in amplifier

The invention claimed is:

1. A double-resonance structure for DNP-NMR and/or ENDOR experiments, comprising a microwave resonator for generating electromagnetic fields suitable for EPR, and comprising an HF resonator for generating electromagnetic fields suitable for NMR,
characterized in that
the HF resonator comprises a plurality of electrically conductive strips together serving as a reflector, each strip characterized by a width, the conductive strips being arranged side by side and electrically connected, so that an HF current can be generated in the plurality of strips, such that the HF currents flow simultaneously in the same direction in the individual strips,
wherein a portion of the HF resonator forms part of the microwave resonator at the same time.

2. The double-resonance structure according to claim 1, wherein the plurality of conductive strips are arranged parallel to one another in the form of a grid.

3. The double-resonance structure according to claim 2, wherein the distance between neighboring conductive strips is smaller than the width of each of the electrically conductive strips and is preferably smaller than half the strip width.

4. The double-resonance structure according to claim 1, wherein the conductive strips are made of a composite material whose magnetic susceptibility is matched to that of a sample to be investigated.

5. The double-resonance structure according to claim 1, wherein at least some of the conductive strips are connected in series by additional conductors.

6. The double-resonance structure according to claim 5, wherein a first end of the series of series-connected strips is connected to ground potential.

7. The double-resonance structure according to claim 6, wherein a second end of the series of series-connected strips is connected or connectable via a capacitor, in particular an adjustable matching capacitor, to an HF source and/or to an HF receiver for generating and/or detecting an NMR signal.

8. The double-resonance structure according to claim 1, wherein the microwave resonator comprises a spherical reflector and a planar reflector for microwaves, these reflectors being opposite one another, such that the planar reflector is formed by a section of the HF resonator.

9. The double-resonance structure according to claim 8, wherein an iris is formed in the spherical reflector, through which microwaves can be fed into the microwave resonator.

10. The double-resonance structure according to claim 9, in which the iris is in the form of a slot to create linearly polarized microwave modes in the microwave resonator.

11. The double-resonance structure according to claim 9, wherein the iris is in the form of a circle to create circularly polarized microwave modes in the microwave resonator.

12. The double-resonance structure according to claim 1, wherein microwaves can be fed into the microwave resonator between conductive strips of the HF resonator.

13. The double-resonance structure according to claim 12, which also comprises a horn radiator which is arranged on the side of the HF resonator facing away from the microwave resonator, so that it can input microwaves through interspaces between conductive strips of the HF resonator into the microwave resonator.

14. The double-resonance structure according to claim 8, wherein the spherical reflector and the HF resonator are designed and arranged so that a $TEM_{00n}$ microwave mode can develop between them.

15. The double-resonance structure according to claim 1, wherein the microwave resonator is connected to a microwave source and can be operated in the lowest radiation mode of the microwave resonator.

16. The double-resonance structure according to claim 1, wherein a location is provided for receiving a sample which is connected to the HF resonator in a thermally conducting manner.

17. The double-resonance structure according to claim 16, wherein the location for receiving a sample comprises a device for receiving a liquid sample.

18. The double-resonance structure according to claim 17, wherein the level of the liquid sample to be held amounts to up to one-tenth of the resonant wavelength of the microwave resonator.

19. The double-resonance structure according to claim 1, which is designed as a probe head which may be inserted into a borehole in a magnet.

20. The double-resonance structure according to claim 19, wherein the probe head has a housing which is connected to ground potential.

21. A DNP-NMR spectrometer, comprising:
a double-resonance structure according to claim 1;
a microwave source coupled to the double-resonance structure for feeding microwaves into the microwave resonator; and
an NMR device coupled to the double-resonance structure for feeding HF signals into the HF resonator and for receiving HF signals from the HF resonator.

22. An ENDOR spectrometer, comprising:
a double-resonance structure according to claim 1;
a microwave source coupled to the double-resonance structure for feeding microwaves into the microwave resonator and for receiving microwaves from the microwave resonator; and
an HF source coupled to the double-resonance structure for feeding HF signals into the HF resonator.

23. A combined DNP-NMR/ENDOR spectrometer, comprising:
a double-resonance structure according to claim 1;
a microwave device, which, in an NMR mode, is suitable for feeding microwave signals into the microwave resonator of the double-resonance structure, and in an ENDOR mode is suitable for feeding microwaves into the microwave resonator of the double-resonance structure and for receiving and detecting microwave signals from the microwave resonator; and
a high-frequency device, which in an NMR mode is suitable for feeding HF signals into the HF resonator of the double-resonance structure, for receiving and detecting HF signals from the HF resonator, and, in an ENDOR mode, is suitable for feeding HF signals into the HF resonator.

24. A method for investigating samples by means of DNP-NMR and/or ENDOR,
wherein a sample is arranged in a double-resonance structure comprising a microwave resonator and an HF resonator, the method comprising:
generating a microwave field by means of the microwave resonator, this field being suitable for inducing EPR transitions in the sample; and
generating an HF field by means of the HF resonator, this field being suitable for inducing NMR transitions in the sample, characterized in that the HF resonator comprises a plurality of conductive strips arranged side by side and together serving as a reflector in which an HF current is generated that flows in the same direction in the individual strips, and a section of the HF resonator forms a part of the microwave resonator at the same time.

25. The method according to claim 24, wherein the microwave resonator comprises a spherical reflector and a planar reflector for microwaves which are opposite one another such that the planar reflector is formed by a second of the HF resonator.

26. The method according to claim 25, wherein an iris through which microwaves can be fed into the microwave resonator is formed in the spherical reflector.

27. The method according to claim 24, wherein a $TEM_{00n}$ mode is generated in the microwave resonator.

28. The method according to claim 24, wherein the sample is liquid.

29. The method according to claim 24, wherein the sample is brought in heat-conducting contact with the HF resonator.

30. The method according to claim 25, wherein the microwaves are fed into the microwave resonator between conductive strips of the HF resonator.

* * * * *